(12) United States Patent
Vietmeier (10) Patent No.: US 10,368,983 B2
(45) Date of Patent: Aug. 6, 2019

(54) COLLAPSIBLE HEART VALVE INCLUDING STENTS WITH TAPERED STRUTS

(71) Applicant: St. Jude Medical, Cardiology Division, Inc., St. Paul, MN (US)

(72) Inventor: Kristopher Henry Vietmeier, Monticello, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 255 days.

(21) Appl. No.: 15/232,974

(22) Filed: Aug. 10, 2016

(65) Prior Publication Data

US 2017/0042673 A1    Feb. 16, 2017

Related U.S. Application Data

(60) Provisional application No. 62/204,075, filed on Aug. 12, 2015.

(51) Int. Cl.
*A61F 2/24* (2006.01)

(52) U.S. Cl.
CPC .... *A61F 2/2418* (2013.01); *A61F 2210/0014* (2013.01); *A61F 2250/0029* (2013.01); *A61F 2250/0036* (2013.01); *A61F 2310/00023* (2013.01)

(58) Field of Classification Search
None
See application file for complete search history.

(56) References Cited

U.S. PATENT DOCUMENTS

| | | | |
|---|---|---|---|
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

Catheter-implanted prosthetic heart valves, Knudsen, L.L., et al., The International Journal of Artificial Organs, vol. 16, No. 5 1993, pp. 253-262.

(Continued)

*Primary Examiner* — Megan Y Wolf
(74) *Attorney, Agent, or Firm* — Lerner, David, Littenberg, Krumholz & Mentlik, LLP (57) ABSTRACT

A prosthetic heart valve includes a collapsible and expandable stent having a proximal end, a distal end, and a plurality of commissure features disposed between the proximal end and the distal end. The stent includes a plurality of struts, selected ones of the struts having multiple widths along their length and being wider adjacent the commissure features than at locations spaced away from the commissure features. A collapsible and expandable valve assembly includes a plurality of leaflets connected to the plurality of commissure features.

7 Claims, 4 Drawing Sheets

(56) References Cited

U.S. PATENT DOCUMENTS

| | | |
|---|---|---|
| 5,855,601 A | 1/1999 | Bessler et al. |
| 5,935,163 A | 8/1999 | Gabbay |
| 5,961,549 A | 10/1999 | Nguyen et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,869,444 B2 | 3/2005 | Gabbay |
| 6,893,460 B2 | 5/2005 | Spenser et al. |
| 6,908,481 B2 | 6/2005 | Cribier |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,374,573 B2 | 5/2008 | Gabbay |
| 7,381,218 B2 | 6/2008 | Schreck |
| 7,452,371 B2 | 11/2008 | Pavcnik et al. |
| 7,524,331 B2 | 4/2009 | Birdsall |
| RE40,816 E | 6/2009 | Taylor et al. |
| 7,585,321 B2 | 9/2009 | Cribier |
| 7,731,742 B2 | 6/2010 | Schlick et al. |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 2002/0036220 A1 | 3/2002 | Gabbay |
| 2003/0009214 A1* | 1/2003 | Shanley .................. A61F 2/91 623/1.15 |
| 2003/0023303 A1 | 1/2003 | Palmaz et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2005/0096726 A1 | 5/2005 | Sequin et al. |
| 2005/0256566 A1 | 11/2005 | Gabbay |
| 2006/0008497 A1 | 1/2006 | Gabbay |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0041978 A1* | 2/2009 | Sogard .................. A61F 2/2412 428/137 |
| 2009/0112309 A1 | 4/2009 | Jaramillo et al. |
| 2009/0138079 A1 | 5/2009 | Tuval et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0100176 A1* | 4/2010 | Elizondo ................ A61F 2/2418 623/2.38 |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2011/0029072 A1 | 2/2011 | Gabbay |
| 2011/0295363 A1* | 12/2011 | Girard .................. A61F 2/2412 623/1.26 |
| 2012/0071969 A1* | 3/2012 | Li ........................ A61F 2/2412 623/2.17 |
| 2012/0303116 A1 | 11/2012 | Gorman, III et al. |
| 2013/0018458 A1* | 1/2013 | Yohanan ............. A61F 2/2418 623/2.18 |
| 2014/0005776 A1* | 1/2014 | Braido ................ A61F 2/2418 623/2.18 |
| 2014/0142693 A1 | 5/2014 | Krivoruchko et al. |
| 2014/0277389 A1 | 9/2014 | Braido et al. |
| 2015/0209140 A1 | 7/2015 | Bell et al. |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| WO | 91/17720 A1 | 11/1991 |
| WO | 97/16133 A1 | 5/1997 |
| WO | 98/32412 A2 | 7/1998 |
| WO | 99/13801 A1 | 3/1999 |
| WO | 01/028459 A1 | 4/2001 |
| WO | 01/49213 A2 | 7/2001 |
| WO | 01/054625 A1 | 8/2001 |
| WO | 01/056500 A2 | 8/2001 |
| WO | 01/076510 A2 | 10/2001 |
| WO | 02/36048 A1 | 5/2002 |
| WO | 02/47575 A2 | 6/2002 |
| WO | 03/047468 A1 | 6/2003 |
| WO | 2005070343 A1 | 8/2005 |
| WO | 06/073626 A2 | 7/2006 |
| WO | 10/008548 A2 | 1/2010 |
| WO | 10/008549 A1 | 1/2010 |

(56) References Cited

FOREIGN PATENT DOCUMENTS

| WO | 10/096176 A1 | 8/2010 |
|---|---|---|
| WO | 10/098857 A1 | 9/2010 |
| WO | 2014203106 | 12/2014 |
| WO | 2015126712 | 8/2015 |

OTHER PUBLICATIONS

Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
Is it Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
"Direct-Access Valve Replacement", Christoph H. Huber, et al., Journal of the American College of Cardiology, vol. 46, No. 2, (Jul. 19, 2005).
"Percutaneous Aortic Valve Implantation Retrograde From the Femoral Artery", John G. Webb et al., Circulation, 2006; 113:842-850 (Feb. 6, 2006).
"Minimally invasive cardiac surgery", M. J. Mack, Surgical Endoscopy, 2006, 20:S488-S492, DOI: 10.1007/s00464-006-0110-8 (presented Apr. 24, 2006).
"Transapical Transcatheter Aortic Valve Implantation in Humans", Samuel V. Lichtenstein et al., Circulation. 2006; 114: 591-596 (Jul. 31, 2006).
"Closed heart surgery: Back to the future", Samuel V. Lichtenstein, The Journal of Thoracic and Cardiovascular Surgery, vol. 131, No. 5, pp. 941-943.
"Transapical approach for sutureless stent-fixed aortic valve implantation: experimental results"; Th. Walther et al., European Journal of Cardio-thoracic Surgery 29 (2006) 703-708 (Jan. 30, 2006).
"Transapical aortic valve implantation: an animal feasibility study"; Todd M. Dewey et al., The annals of thoracic surgery 2006; 82: 110-6 (Feb. 13, 2006).
Textbook "Transcatheter Valve Repair", 2006, pp. 165-186.
International Search Report for International Patent Application No. PCT/US2016/046251 dated Dec. 5, 2016.

\* cited by examiner

FIG. 1

(PRIOR ART)

COLLAPSIBLE HEART VALVE INCLUDING STENTS WITH TAPERED STRUTS

CROSS-REFERENCE TO RELATED APPLICATIONS

The present application claims the benefit of the filing date of U.S. Provisional Patent Application No. 62/204,075 filed Aug. 12, 2015, the disclosure of which is hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves including stents with tapered struts for fatigue resistance.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implantation site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

There is a need for further improvements to collapsible prosthetic heart valves, and in particular, self-expanding prosthetic heart valves, and to the systems for implanting same. Among other advantages, the present invention may address one or more of these needs.

SUMMARY OF THE INVENTION

In some embodiments, a prosthetic heart valve may include a collapsible and expandable stent having a proximal end, a distal end, and a plurality of commissure features disposed between the proximal end and the distal end, the stent including a plurality of struts, selected ones of the struts having multiple widths along their length and being wider adjacent the commissure features than at select locations spaced away from the commissure features, and a collapsible and expandable valve assembly, the valve assembly including a plurality of leaflets connected to the plurality of commissure features.

In some embodiments, a stent for a prosthetic heart valve having a proximal end and a distal end may include a plurality of commissure features disposed between the proximal end and the distal end, and a plurality of struts, selected ones of the struts having multiple widths along their length and being wider adjacent the commissure features than at select locations spaced away from the commissure features.

BRIEF DESCRIPTION OF THE DRAWINGS

Various embodiments of the present invention are described herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. Also, as used herein, the words "substantially," "approximately," "generally" and "about" are intended to mean that slight variations from absolute are included within the scope of the structure or process recited.

Figure 1:
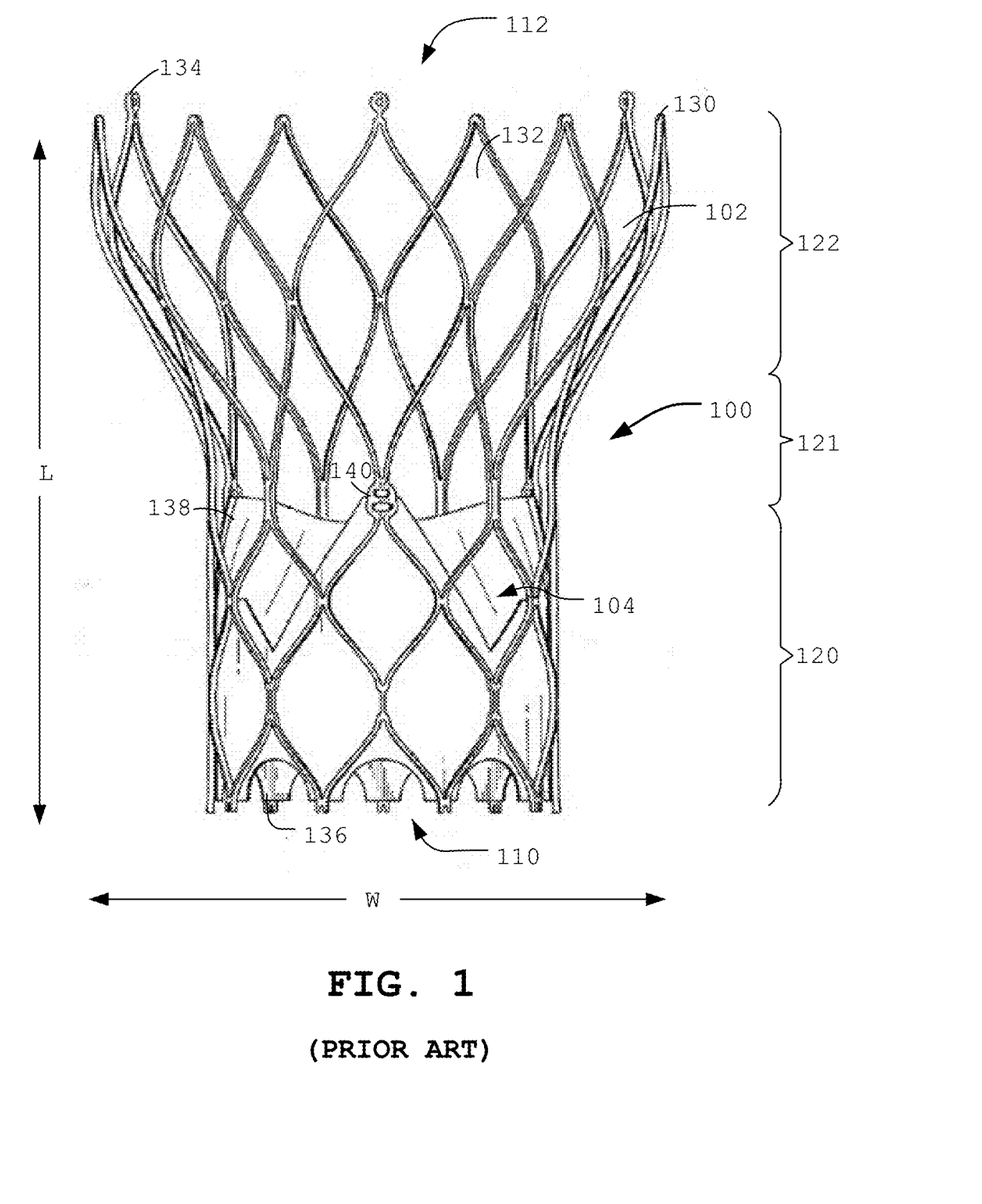
FIG. 1 is a partial side elevational view of a prosthetic heart valve including a valve assembly and a stent.

FIG. 1 shows a collapsible prosthetic heart valve 100 including a collapsible stent 102 and a valve assembly 104. Prosthetic heart valve 100 is designed to replace a native tricuspid valve of a patient, such as a native aortic valve. It should be noted that while the devices disclosed herein are described predominantly in connection with their use to replace a native aortic valve, and are described as having a stent with a shape as illustrated in FIG. 1, the valve could be a bicuspid or other valve, such as the mitral valve, and the stent could have a shape that differs from that shown.

The expandable stent 102 of prosthetic heart valve 100 may be formed from biocompatible materials that are capable of self-expansion, such as, for example, shape-memory alloys, such as the nickel-titanium alloy known as "nitinol," or other suitable metals or polymers. Stent 102 extends in a length direction L from proximal or annulus end 110 to distal or aortic end 112, and includes annulus section 120 adjacent proximal end 110, transition section 121, and aortic section 122 adjacent distal end 112. Annulus section 120 has a relatively small cross-section in the expanded condition, while aortic section 122 has a relatively large cross-section in the expanded condition. Preferably, annulus section 120 is in the form of a cylinder having a substantially constant diameter along its length. Transition section 121 may taper outwardly from annulus section 120 to aortic section 122. Stent 102 may also have different shapes, such as a flared or conical annulus section, a less bulbous aortic section, and the like, and a differently shaped transition section 121. Each of the sections of stent 102 may be laser cut from a tube to create a plurality of struts 130 forming cells 132 connected to one another in one or more annular rows around the stent. For example, as shown in FIG. 1, annulus section 120 may have two annular rows of complete cells 132 and aortic section 122 and transition section 121 may each have one or more annular rows of partial cells 132. Cells 132 in aortic section 122 may be larger than cells 132 in annulus section 120 to better enable prosthetic valve 100 to be positioned in the native valve annulus without the stent structure interfering with blood flow to the coronary arteries. Each of cells 132 has a length in length direction L of the stent and a width in a perpendicular direction W.

Stent 102 may include one or more retaining elements 134 at distal end 112 thereof, retaining elements 134 being sized and shaped to cooperate with corresponding recesses in a retainer of a device for delivering prosthetic heart valve 100 into a patient. The engagement of retaining elements 134 with the retainers of the delivery device helps maintain prosthetic heart valve 100 in assembled relationship with the delivery device, minimizes longitudinal movement of the prosthetic heart valve relative to the delivery device during unsheathing or resheathing procedures, and helps prevent rotation of the prosthetic heart valve relative to the delivery device as the delivery device is advanced to the target location and the heart valve deployed.

Valve assembly 104 of prosthetic heart valve 100 preferably is positioned in annulus section 120 of stent 102 and secured to the stent. Valve assembly 104 includes cuff 136 and a plurality of leaflets 138 which collectively function as a one way valve by coapting with one another. As a prosthetic aortic valve, valve 100 has three leaflets 138.

Although cuff 136 is shown in FIG. 1 as being disposed on the luminal or inner surface of annulus section 120, it is contemplated that cuff 136 may be disposed on the abluminal or outer surface of annulus section 120 or may cover all or part of either or both of the luminal and abluminal surfaces. Both cuff 136 and leaflets 138 may be wholly or partly formed of any suitable biological material or polymer such as, for example, polytetrafluoroethylene (PTFE).

Leaflets 138 may be attached along their belly portions to cuff 136 and/or to stent 102, with the commissure between adjacent leaflets 138 being attached to a commissure feature 140. As can be seen in FIG. 1, each commissure feature 140 may lie at the intersection of four cells 132, two of the cells being adjacent one another in the same annular row, and the other two cells being in different annular rows and lying in end to end relationship. Preferably, commissure features 140 are positioned entirely within annulus section 120 or at the juncture of annulus section 120 and transition section 121. Commissure features 140 may include one or more eyelets which facilitate the suturing of the leaflet commissure to stent 102. In at least some examples, commissure features 140 may include one, two, three, four, five or six or more eyelets arranged in rows and/or columns. The eyelets may be formed of the same shape and/or size and sutures may be passed through any combination of the eyelets as desired.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside a compartment of a delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 120 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Figure 2:
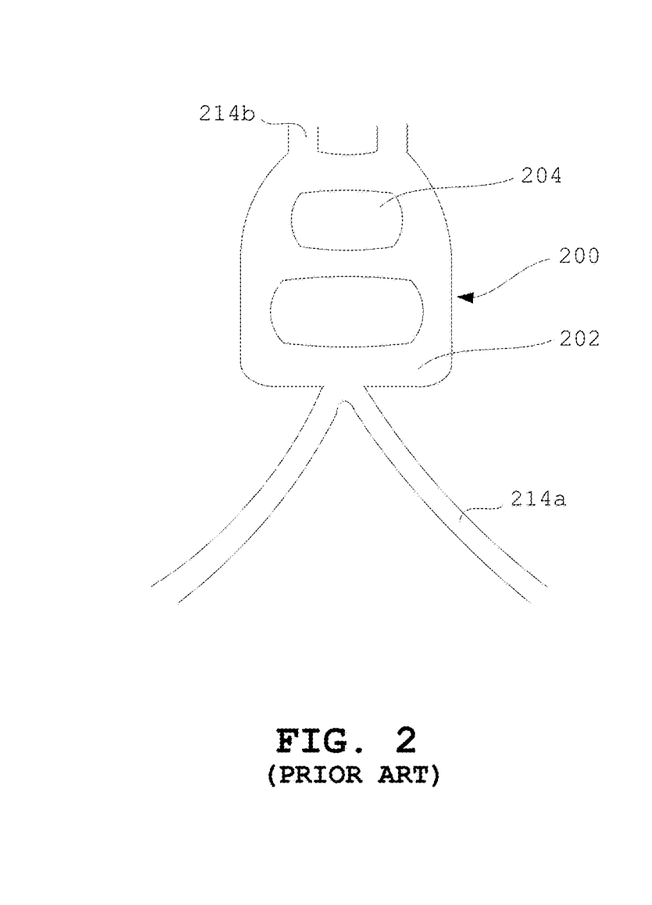
FIG. 2 is an enlarged, schematic side view of a commissure feature of a prosthetic heart valve showing.

FIG. 2 illustrates one version of a commissure feature 200 coupled to prior struts 214a,214b for attaching a valve assembly to the stent. Commissure feature 200 has a body 202 with a pair of eyelets 204. Leaflets (not shown) may be attached via sutures, staples, glue or any other suitable means to commissure feature 200, such as by passing sutures through eyelets 204 and wrapping them around struts 214a, 214b. The load exerted on the commissure feature 200 by the attached leaflets is distributed across the entire area of commissure feature 200.

Figure 3:
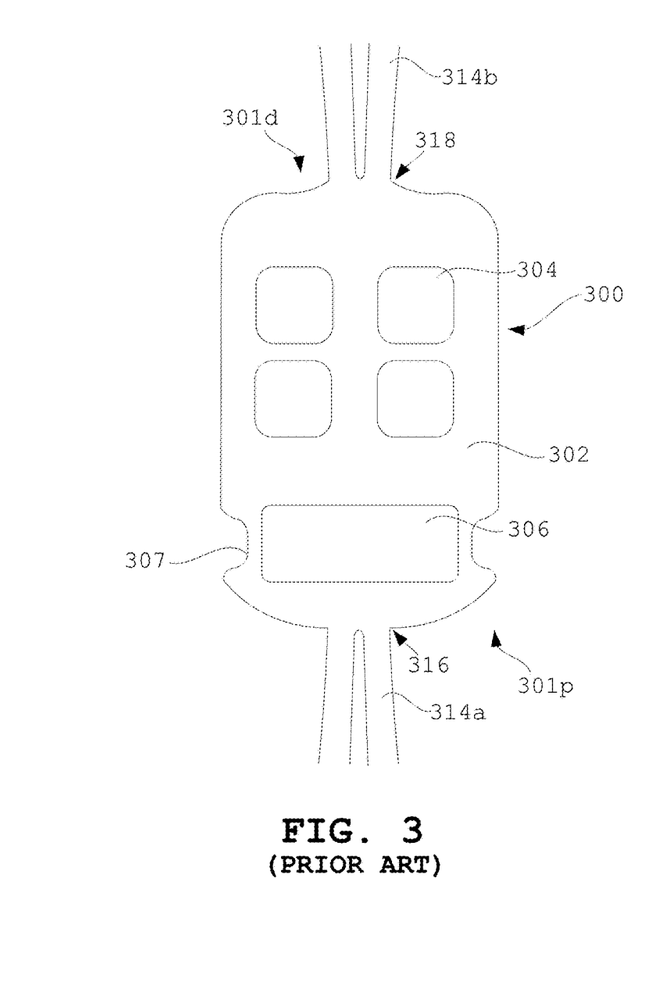
FIG. 3 is an enlarged, schematic side view of another commissure feature.

FIG. 3 illustrates a commissure feature 300 coupled to prior art struts 314a,314b. Commissure feature 300 has a body 302 extending between proximal end 301p and distal end 301d, the body having a plurality of substantially square eyelets 304 arranged in rows and/or columns, and an elongated eyelet 306 disposed adjacent proximal end 301p. Body 302 further includes a pair of notches 307 for receiving sutures. Leaflets (not shown) may be attached via sutures, glue, staples or any suitable means to commissure feature 300, such as by passing sutures through eyelets 304,306 and by wrapping the sutures around struts 314a,314b. Stress from the leaflets is distributed across the entire area of the commissure feature 300. Because commissure feature 300 has a larger overall area than commissure feature 200, commissure feature 300 provides a larger area across which the stress from the leaflets is distributed when compared to the area of commissure feature 200. A larger area for distributing loads may decrease the chance of leaflet failure at the commissure feature-leaflet attachment.

As shown in FIG. 3, struts 314a are coupled to body 302 adjacent proximal end 301p and struts 314b are coupled to body 302 adjacent distal end 301d. A first intersection 316 is formed at the junctions between struts 314a and body 302, and a second intersection 318 is formed at the junctions between struts 314b and body 302, the intersections being in the form of abrupt transitions forming approximately a right angle between struts 314a,314b and body 302. As a result of these abrupt transitions, intersections 316, 318 act as stress concentrators, such that the stresses acting on commissure feature 300 from the leaflets may be concentrated at these intersections. The excess stress at intersections 316,318 and adjacent portions of the stent may make them prone to failure due to fatigue.

Figure 4A:
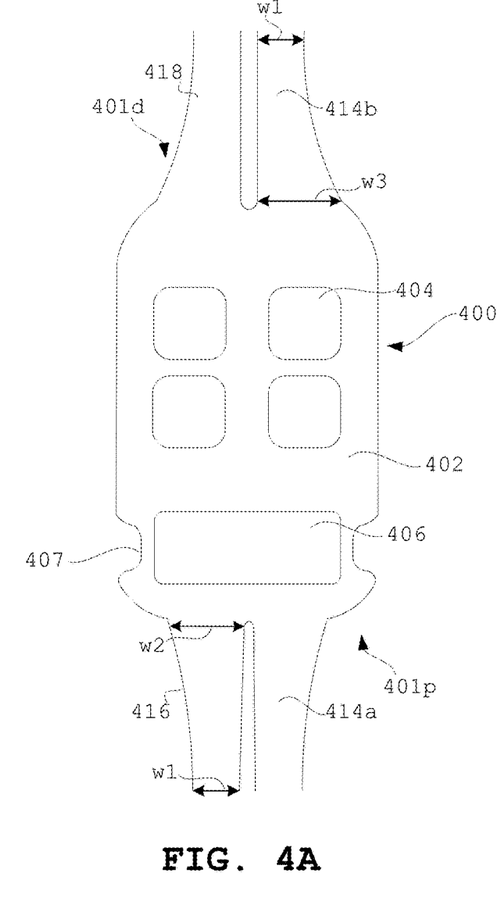
FIG. 4A is an enlarged, schematic side view of a commissure feature having tapered struts.

FIG. 4A illustrates a commissure feature 400 coupled to tapered struts 414a,414b according to one embodiment of the present disclosure. Commissure feature 400 has a body 402 extending between proximal end 401p and distal end 401d, the body having a plurality of substantially square eyelets 404 arranged in rows and/or columns, and an elongated eyelet 406 disposed adjacent proximal end 401p. Body 402 further includes a pair of notches 407 for receiving sutures. Leaflets (not shown) may be attached via sutures, glue, staples or any suitable means to commissure feature 400. For example, the attachment may be made by passing sutures through the leaflets and through eyelets 404, 406 of commissure feature 400 and wrapping them around struts 414a, 414b.

Figure 4B:
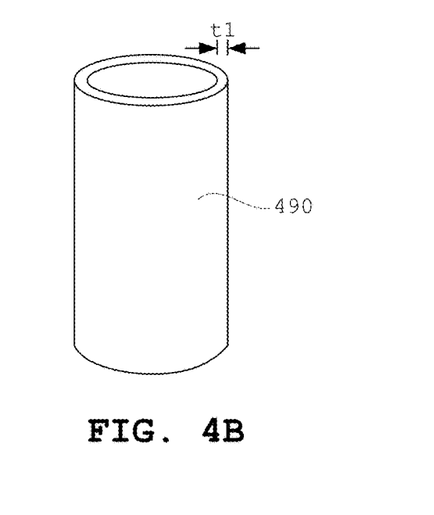
FIG. 4B illustrates a tube from which a stent will be cut.

Struts 414a are coupled to body 402 adjacent proximal end 401p and struts 414b are coupled to body 402 adjacent distal end 401d. In order to enhance the durability of the stent adjacent the commissure features, tapered struts 414a, 414b gradually increase in width toward the commissure feature. For example, struts 414a may have a first width w1 at a spaced distance from commissure feature 400 that is approximately 0.25 mm, and a second width w2 immediately adjacent commissure feature 400 that is approximately 0.5 mm, the second width w2 being the widest portion of the strut. Additionally, in some embodiments, width w1 is approximately one-half or one-third of width w2. The majority of each strut 414a may have the first width w1, with only a small portion of the strut having a width that is greater than w1. In at least some examples, approximately 70% to approximately 80% of each strut 414a has the first width w1, with the remaining portion having widths that gradually increase until reaching width w2. A smooth curve 416 is defined along the outside edge of each strut 414a between first width w1 and second width w2. Smooth curve 416 may have a single radius of curvature or multiple radii. The gradual increase in width along curve 416 provides a generally smooth transition from strut 414a to body 402 such that an obtuse angle of between about 120 degrees and about 170 degrees is formed therebetween. The obtuse angle between struts 414a and body 402 reduces the stress concentration at the intersection therebetween from that exhibited by the arrangement shown in FIG. 3. As seen in FIG. 4B, a stent may be laser cut from a tube 490 having a wall thickness ti into a plurality of struts forming cells as shown in FIG. 1. After laser cutting, the thickness of each strut will be equal to the initial wall thickness ti of the tube. Width w1 may be less than or equal to the thickness ti of the struts, while width w2 may be greater than the thickness ti of the struts.

Likewise, strut 414b may have a first width w1 that is approximately equal to the first width of strut 414a, and a third width w3 immediately adjacent commissure feature 400 that is between about 0.25 and about 0.3 mm, the third width w3 being the widest portion of the strut. The majority of each strut 414b may have the first width w1, with only a small portion of the strut having a width that is greater than w1. In at least some examples, approximately 70% to approximately 80% of strut 414b has the first width w1 with the remaining portion having gradually increasing widths until width w3.

A second smooth curve 418 is defined along the outside edge of each strut 414b between first width w1 and third width w3, the gradual increase in width along curve 418 providing a generally smooth transition from strut 414b to body 402 such that an obtuse angle of at least between about 120 degrees and about 170 degrees is formed therebetween. Smooth curve 418 may have a single radius of curvature or multiple radii. In at least some examples, a curve is formed from width w1 to width w3, the curve having a radius of curvature of about 5 mm to about 75 mm.

It will be understood that the curvatures and widths discussed herein are merely exemplary and not to be taken as limiting. For example, struts 414a have been described as being coupled to body 402 adjacent proximal end 401p, but the widths and/or curvatures associated with each of struts 414a need not be the same (e.g., only one of struts 414a may include an increased width, or one of the struts may be wider than another of struts 414a). Likewise, struts 414b have been described as being coupled to body 402 adjacent distal end 401d, but the widths and/or curvatures associated with each of struts 414b need not be the same (e.g., only one of struts 414b may include an increased width, or one of the struts may be wider than another of struts 414b). Moreover, upper struts 414a and lower 414b may have different curvatures and/or widths from each other.

Without being bound by any particular theory, it is believed that fatigue performance of a strut is at least partly determined by the overall dimensions of the stent (e.g., strut width, strut thickness, strut length, cell density. Fatigue resistance may also need to be balanced with the radial force exerted by or on the stent. For example, increasing the width of the struts may increase the fatigue resistance of the strut, but at the same time it may reduce the crimpability of the stent and/or increase the radial force exerted by the stent on body tissue when implanted. By providing a gradually increasing strut width at only preselected locations, fatigue performance may be improved at high strain areas, while the stents chronic outward force may be optimized.

Thus, a predetermined curvature or curvatures may be formed at certain regions of the struts that couple to a commissure feature, providing those struts with a gradually increasing width closer to the commissure feature. Moreover, such a curvature may be implemented on all struts that join to a commissure feature, or on only certain struts that experience high strain (e.g., only struts 414a, only struts 414b or some combination of the two). Additionally, curvature may be implemented in struts that join to commissure features that are not generally rectangular (e.g., the egg-shaped commissure of FIG. 2).

Figure 5A:
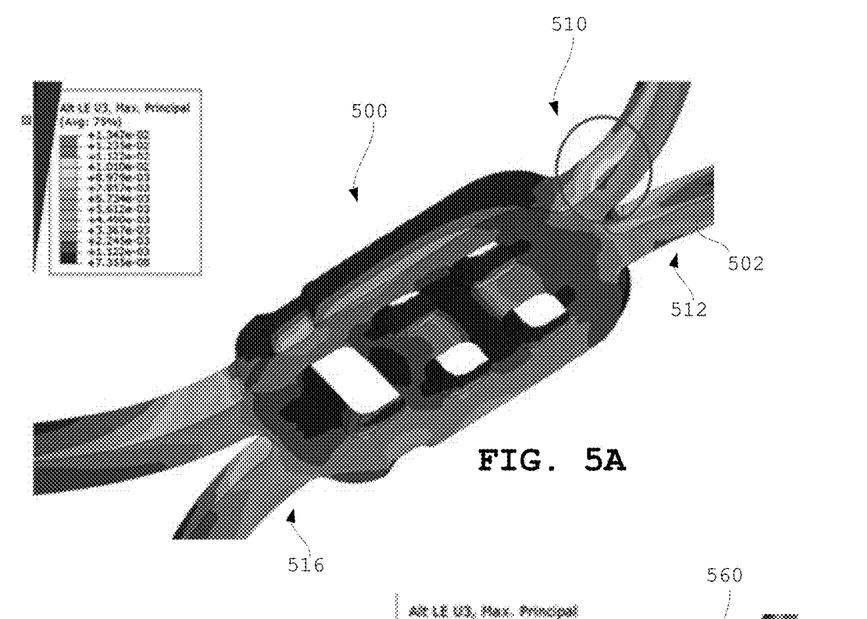
FIG. 5A is an enlarged, schematic perspective view showing the strain on a commissure feature not having tapered struts.

In order to appreciate the differences in fatigue resistance between stents having tapered struts and stents without tapered struts, a finite element analysis was conducted. The analysis was conducted on a stent having commissures 500 connected to struts 502 without tapers and the alternating strain and associated mean strain was measured at three locations as shown below in Table 1.

In Tables 1 and 2, reference to a location "above" the commissure refers to a location distal to the commissure, and reference to a location "below" the commissure refers to a location proximal to the commissure.

TABLE 1

| Stent with Struts Without a Taper | | |
|---|---|---|
| Location | Alternating Strain (%) | Associated Mean Strain (%) |
| Above commissure (512) | 1.35 | 1.65 |
| One strut below commissure (not shown) | 0.80 | 1.86 |
| Below commissure (516) | 0.79 | 2.71 |

As will be appreciated from FIG. 5A and Table 1, regions of the stent above commissure feature 500, such as region 510 of strut 502, are prone to failure due to high strain. No appreciable strain was measured at the commissure notch.

Figure 5B:
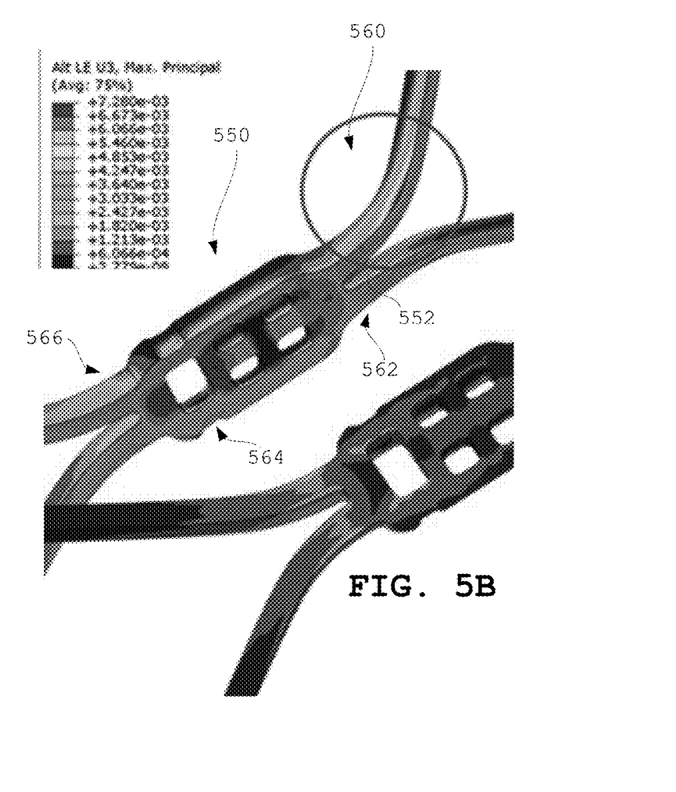
FIG. 5B is an enlarged, schematic perspective view showing the strain on a commissure feature having tapered struts.

A second analysis was conducted on a stent having commissures 550 connected to struts 552 that are tapered as described with reference to FIG. 4A and the alternating strain and associated mean strain was measured at four locations as shown below in Table 2.

TABLE 2

Stent with Struts Having a Taper

| Location | Alternating Strain (%) | Associated Mean Strain (%) |
|---|---|---|
| Above commissure (562) | 0.73 | 0.88 |
| One strut below commissure (not shown) | 0.61 | 1.10 |
| Commissure notch (564) | 0.59 | 0.48 |
| Below commissure (566) | 0.44 | 0.76 |

As will be appreciated from FIG. 5B and Table 2, a reduced strain is apparent in certain regions of the stent, such as region 560 of strut 552. Specifically, the inclusion of tapers in the form of curved edges as described above with reference to FIG. 4A permits the distribution of strain over a larger area, reducing strain concentration in discrete areas. Moreover, because the increase in width is merely local (e.g., along discrete portions of a strut), the performance of the device (e.g., crimpability of the stent, anchoring of the stent, etc.) is not affected. Additionally, it will be noted that the preceding embodiments may result in a reduction in maximum strain within the stent.

Although the invention herein has been described with reference to particular embodiments, it is to be understood that these embodiments are merely illustrative of the principles and applications of the present invention. For example, the tapering of struts may be utilized in any area in addition to, or instead of, areas discussed above that are adjacent to a commissure attachment feature. In fact, in at least some examples, tapered struts are formed in stents having no commissure features. Thus, struts may be tapered as described above adjacent areas of high strain to reduce the peak strain in those areas. It is therefore to be understood that numerous modifications may be made to the illustrative embodiments and that other arrangements may be devised without departing from the spirit and scope of the present invention as defined by the appended claims. It will be appreciated that the various dependent claims and the features set forth therein can be combined in different ways than presented in the initial claims. It will also be appreciated that the features described in connection with individual embodiments may be shared with others of the described embodiments.

In some embodiments, a prosthetic heart valve may include a collapsible and expandable stent having a proximal end, a distal end, and a plurality of commissure features disposed between the proximal end and the distal end, the stent including a plurality of struts, selected ones of the struts having multiple widths along their length and being wider adjacent the commissure features than at select locations spaced away from the commissure features, and a collapsible and expandable valve assembly, the valve assembly including a plurality of leaflets connected to the plurality of commissure features; and/or each of the selected ones of the struts may be coupled to one of the commissure features at a junction, each of the selected ones of the struts being widest at the junction; and/or the selected ones of the struts may include proximal struts coupled to a proximal end of one of the commissure features; and/or each of the proximal struts has a first width at a spaced distance from commissure feature; and/or each of the proximal struts has a second width adjacent the commissure feature that is approximately twice as wide as the first width; and/or the first width may be less than a thickness of each of the proximal struts and the second width may be greater than the thickness of each of the proximal struts; and/or each of the proximal struts may have a first width, and a second width that is greater than the first width, approximately 70% to approximately 80% of a length of each of the proximal struts having the first width and a remaining portion of the length of each of the proximal struts having widths that gradually increase from the first width to the second width; and/or the selected ones of the struts may include distal struts coupled to a distal end of one of the commissure features; and/or each of the distal struts has a first width at a spaced distance from the distal end of the one commissure feature that is about 0.25 mm; and/or wherein each of the distal struts has another width adjacent the distal end of the one commissure feature that is about 0.5 mm; and/or the first width may be less than a thickness of each of the distal struts and the another width may be greater than the thickness of each of the distal struts; and/or each of the distal struts may have a first width, and a third width that is greater than the first width, approximately 70% to approximately 80% of a length of each of the distal struts having the first width and a remaining portion of the length of each of the distal struts having widths that gradually increase from the first width to the third width; and/or the selected ones of the struts may be tapered with a gradual curvature that provides a generally smooth transition to a body of the commissure feature, the smooth transition having a notch for accepting a suture; and/or each of the commissure features may include a body that is substantially rectangular.

In other embodiments, a stent for a prosthetic heart valve having a proximal end and a distal end may include a plurality of commissure features disposed between the proximal end and the distal end, and a plurality of struts, selected ones of the struts having multiple widths along their length and being wider adjacent the commissure features than at select locations spaced away from the commissure features; and/or each of the selected ones of the struts may be coupled to one of the commissure features at a junction, each of the selected ones of the struts being widest at the junction; and/or the selected ones of the struts include proximal struts coupled to a proximal end of one of the commissure features; and/or the selected ones of the struts include distal struts coupled to a distal end of one of the commissure features; and/or the selected ones of the struts have a first width and a second width, the first width being less than a thickness of each of the selected ones of the struts and the second width being greater than the thickness of each of the selected ones of the struts; and/or the selected ones of the struts are tapered with a gradual curvature that provides a generally smooth transition to a body of the commissure feature, the smooth transition having a notch for accepting a suture.

The invention claimed is:

1. A prosthetic heart valve, comprising:
a collapsible and expandable stent having an annulus section adjacent a proximal end, an aortic section adjacent a distal end, a transition section tapering outwardly from the annulus section to the aortic section, and a plurality of commissure features disposed between the proximal end and the distal end, the stent including a plurality of struts, selected ones of the struts being directly coupled to one of the plurality of commissure features and having multiple widths along their length and being wider adjacent the one of the plurality of commissure features than at select locations spaced away from the one of the plurality of commissure features; and a collapsible and expandable valve assembly, the valve assembly including a plurality of leaflets, two adjacent leaflets forming a leaflet commissure directly connected to the one of the plurality of commissure features, the valve assembly configured to allow blood to flow from the annulus section toward the aortic section and to prevent blood from flowing from the aortic section to the annulus section, wherein the selected ones of the struts include a first pair of proximal struts each coupled to a proximal end of the one of the plurality of commissure features at a proximal junction and extending within the annulus section toward the proximal end of the stent, and a second pair of distal struts each coupled to a distal end of the one of the plurality of commissure features at a distal junction and extending within the transition section toward the distal end of the stent;

wherein each of the proximal struts has a first width at a spaced distance from the one of the plurality of commissure features;

wherein each of the proximal struts has a second width adjacent the one of the plurality of commissure features that is approximately twice as wide as the first width; and wherein the first width is less than a thickness of each of the proximal struts and the second width is greater than the thickness of each of the proximal struts.

2. The prosthetic heart valve of claim 1, wherein each of the first pair of proximal struts is widest at the proximal junction and each of the second pair of distal struts is widest at the distal junction.

3. The prosthetic heart valve of claim 1, wherein approximately 70% to approximately 80% of the length of each of the proximal struts has the first width and a remaining portion of the length of each of the proximal struts has widths that gradually increase from the first width to the second width.

4. The prosthetic heart valve of claim 1, wherein each of the distal struts has a first distal strut width, and a third width that is greater than the first distal strut width, approximately 70% to approximately 80% of the length of each of the distal struts having the first distal strut width and a remaining portion of the length of each of the distal struts having widths that gradually increase from the first distal strut width to the third width.

5. The prosthetic heart valve of claim 1, wherein each of the proximal struts are tapered with a gradual curvature that provides a generally smooth transition to a body of the one of the plurality of commissure features, the generally smooth transition being adjacent a notch in the body, the notch for accepting a suture.

6. The prosthetic heart valve of claim 1, wherein each of the plurality of commissure features includes a body that is substantially rectangular.

7. A prosthetic heart valve, comprising:

a collapsible and expandable stent having an annulus section adjacent a proximal end, an aortic section adjacent a distal end, a transition section tapering outwardly from the annulus section to the aortic section, and a plurality of commissure features disposed between the proximal end and the distal end, the stent including a plurality of struts, selected ones of the struts being directly coupled to one of the plurality of commissure features and having multiple widths along their length and being wider adjacent the one of the plurality of commissure features than at select locations spaced away from the one of the plurality of commissure features; and a collapsible and expandable valve assembly, the valve assembly including a plurality of leaflets, two adjacent leaflets forming a leaflet commissure directly connected to the one of the plurality of commissure features, the valve assembly configured to allow blood to flow from the annulus section toward the aortic section and to prevent blood from flowing from the aortic section to the annulus section, wherein the selected ones of the struts include a first pair of proximal struts each coupled to a proximal end of the one of the plurality of commissure features at a proximal junction and extending within the annulus section toward the proximal end of the stent, and a second pair of distal struts each coupled to a distal end of the one of the plurality of commissure features at a distal junction and extending within the transition section toward the distal end of the stent;

wherein each of the distal struts has a first width at a spaced distance from the distal end of the one of the plurality of commissure features that is about 0.25 mm;

wherein each of the distal struts has another width adjacent the distal end of the one of the plurality of commissure features that is about 0.5 mm; and wherein the first width is less than a thickness of each of the distal struts and the another width is greater than the thickness of each of the distal struts.

* * * * *